United States Patent
Möller-Bremer

(10) Patent No.: US 6,281,002 B1
(45) Date of Patent: Aug. 28, 2001

(54) METHOD FOR PRESERVING AQUEOUS SOLUTIONS OR DISPERSIONS

(75) Inventor: Christine Möller-Bremer, Nordholz (DE)

(73) Assignee: Lumos Trading & Investments Corporation (VG)

( * ) Notice: Subject to any disclaimer, the term of this patent is extended or adjusted under 35 U.S.C. 154(b) by 0 days.

(21) Appl. No.: 08/490,280

(22) Filed: Jun. 14, 1995

(30) Foreign Application Priority Data

Jun. 20, 1994 (DE) ................................. 44 21 504

(51) Int. Cl.⁷ .............................. B09B 3/00; C02F 3/00; C12N 1/20; D21C 5/02
(52) U.S. Cl. .............................. 435/262.5; 162/4; 162/5; 210/601; 435/264; 435/267; 435/822
(58) Field of Search ................................. 435/260, 262.5, 435/263, 267, 282, 821, 822; 210/601; 162/4, 5

(56) References Cited

U.S. PATENT DOCUMENTS

| | | | |
|---|---|---|---|
| 3,949,086 | * | 4/1976 | Wolfson .............................. 424/302 |
| 4,028,394 | * | 6/1977 | Karsten et al. .................. 260/455 A |
| 4,250,264 | * | 2/1981 | Nelson et al. ........................ 435/253 |
| 4,872,986 | * | 10/1989 | Stringfellow et al. ............... 210/611 |
| 5,242,593 | * | 9/1993 | Oberkofler et al. ................. 210/606 |
| 5,256,182 | * | 10/1993 | Friedman, Jr. et al. ............. 504/124 |
| 5,439,678 | * | 8/1995 | Dobrogosz et al. .............. 424/93.45 |
| 5,597,565 | * | 1/1997 | Leifert et al. ........................ 424/115 |

FOREIGN PATENT DOCUMENTS

| | | | |
|---|---|---|---|
| 38 25 312 | * | 2/1990 | (DE) . |
| 41 27 744 | * | 2/1993 | (DE) . |
| 236989 | * | 9/1987 | (EP) . |
| 372520 | * | 6/1990 | (EP) . |
| 558360 | * | 9/1993 | (EP) . |
| 2102037 | * | 3/1972 | (FR) . |
| 2654437 | * | 5/1991 | (FR) . |
| WO93/09671 | * | 5/1993 | (WO) . |

* cited by examiner

Primary Examiner—Jon P. Weber
Assistant Examiner—Deborah K. Ware
(74) Attorney, Agent, or Firm—Fay, Sharpe, Fagan, Minnich & McKee, LLP

(57) ABSTRACT

The invention relates to a method for preserving aqueous solutions or dispersions containing organic substances, and to an apparatus for carrying out this method and the application of the method. Also a method of preserving aqueous solutions or dispersions comprising glue or starch is disclosed.

10 Claims, No Drawings

METHOD FOR PRESERVING AQUEOUS SOLUTIONS OR DISPERSIONS

BACKGROUND OF THE INVENTION

1. Field of the Invention

This invention relates to a method for preserving aqueous solutions or dispersions containing organic substances which are degraded by microorganisms present as impurities. The invention also relates to a plant for carrying out this method and to applications of the method.

2. Description of the Related Art

There are a number of materials which must be held in aqueous solution or dispersion to facilitate their production and handling, their transport and storage as well as their application by the consumer. Such materials or products are required in particular in branches of industry like the paper and pulp industry. They include pigments, fillers, paper machine broke, starch, glue or retention agents, for example, which can all be prepared in the form of aqueous solutions or dispersions.

Microorganisms which are always present as contamination find optimal living conditions in this aqueous milieu. Owing to the high organic and inorganic nutrient offer and a favorable milieu with respect to temperature and pH value, such microorganisms show increased and quick growth.

Such solutions or dispersions always also contain other organic substances which are imported with the raw materials during preparation of the aqueous solutions or dispersions. Starch and glue as well as the composition of paper machine broke themselves constitute food for certain species of microorganisms.

With the increased growth of such microorganisms the organic substances present as contamination are increasingly degraded at the same time, which produces a change in the product-specific properties of the liquid product.

There are essentially two different conditions under which these aqueous liquid products are usually handled and which have a strong influence on the type of microbial growth and thus the microbial activity.

Under the first condition the liquid products are mixed continuously or at regular intervals under aerobic conditions. The air or oxygen feed this involves promotes the growth of particularly aerobic microorganisms. Such conditions are found particularly in systems where starch or glue are produced, or in broke pulpers and in the storage tanks or transport tanks for such products. One consequence of the increasing microbial contamination here is slime formation and deposit and a change in the desired specific product properties like viscosity, pH value, color and brightness.

Under the second condition the aqueous liquid products are not stirred but stored in tanks largely sealed off from air or oxygen. After a short initial phase in which the oxygen introduced during filling is consumed by the existing microorganisms, anaerobic microorganisms grow here. Owing to their metabolism these anaerobically respiring microorganisms release hydrogen ions which reduce nitrate, sulfate, sulfur and carbonates into nitrite, hydrogen sulfide, methane, acetic acid or other highly reduced compounds (Basic Biotechnology—A Student's Guide, P. Präve, U. Faust, W. Sittig, D. A. Sukatsch, VCH Verlagsgesellschaft Weinheim, 1987, page 101).

Anaerobically respiring microorganisms can therefore cause serious problems in particular with regard to the transport and storage of liquid products.

As already mentioned, these microorganisms release hydrogen ions which for their part have a reducing effect on certain substances which are either part of the liquid product or contained therein as contamination. For example, the reduction of sulfate or sulfur gives rise to sulfide in the form of hydrogen sulfide. Hydrogen sulfide is not only highly toxic, it is also more than undesirable because of its smell of rotten eggs and its property of discoloring products. Other reduction products like nitrite, methane or acetic acid also lead to an undesirable change in specific product properties, for example the brightness and smell of broke or crude fiber suspension, and the color and smell of finished paper.

To prevent, or at least check, the increase in microbial contamination and the related degradation or breakdown of organic substances present in the liquid products, few possibilities were available up to now.

One possibility is to use up the solution or dispersion very quickly before microbial degradation begins. This approach is only applicable to a limited extent since microbial degradation already sets in after a few hours under the usual optimal conditions. This possibility is practicable for example in connection with broke which is processed quickly, but totally unsuitable for example for conserving the stability of pigment slurries.

A further possibility is to store the aqueous liquid products under conditions which do not permit growth of the microorganisms. Such conditions are for example very high or very low temperatures. Both are very difficult to attain under practical conditions, and are most likely to be found in a starch digester or in storing starch.

A further possibility is to suppress, or completely eliminate, the growth of microorganisms by adding biocides. But only a limited number of biocides are effective against anaerobically respiring, in particular sulfate-reducing, microorganisms, and the latter are regarded as the worst form of contamination. Furthermore, the use of biocides meets increasingly with discredit. Although many of the biocides used in the paper industry are degraded very quickly, they are nevertheless dangerous for man and the environment if they go outside their normal area of use, for example due to a transport accident. Also, microorganisms are very likely to develop resistance to biocides and this can only be avoided by frequently changing the biocide or increasing the dose. Some biocides also contain halogens and thus contribute to the potential influence of absorbable organic halogens (AOX) on the environment. Many paper and pulp mills furthermore have biological clarification plants which can be greatly affected by improper handling of biocides.

A further possibility of controlling the growth of microorganisms in liquid products is to add strong oxidizing and bleaching agents. Oxidizing agents like hydrogen peroxide act very reliably, but their handling is very problematic not least because of the danger of corrosion. Such products are furthermore expensive, and treatment must take place continuously since the hydrogen peroxide is exhausted quickly. The same holds for bleaching agents like hypochlorite and bromochlorohydantoin. The latter furthermore contribute to increasing the AOX values in the finished product.

The problem of the present invention is therefore to provide a non-polluting method for preserving aqueous solutions and/or dispersions which is industrially applicable and reliably prevents microbial degradation of organic substances contained in these liquid products. The idea of the invention is to prevent the growth of such microorganisms by depriving them of their basis for food.

SUMMARY OF THE INVENTION

The subject of the invention is a method for preserving aqueous solutions or dispersions containing organic substances which are degraded by living microorganisms, which is characterized by the fact that one adds to the solutions or dispersions microorganisms which inhibit the growth of microorganisms causing degradation.

Surprisingly enough the application of the inventive method, namely the addition of selected specific microorganisms to aqueous solutions or dispersions (emulsions, suspensions), produces a strong and long-lasting preservation effect which is based on the suppression of undesirable microbial growth of microorganisms degrading organic substances. This is all the more surprising since the addition of microorganisms initially causes an increase in the organic load and germ count.

The inventive method shows a non-polluting way of treating a number of liquid products to avoid undesirable microbial degradation and a resulting loss of product-specific properties like brightness, color, smell and corrosiveness of the tanks.

DESCRIPTION OF THE PREFERRED EMBODIMENTS

The microorganisms which are added to a liquid product sealed off from air or oxygen can advantageously be selected so that they inhibit the growth of anaerobically respiring microorganisms. This is especially of advantage if these anaerobically respiring microorganisms have sulfate-reducing properties since it rules out the formation of hydrogen sulfide. As mentioned, hydrogen sulfide is not only toxic but also smells bad and causes a musty smell and undesirable color change in the final product.

The microorganisms used for inhibiting the growth of degrading microorganisms are advantageously selected from the group consisting of bacteria and fungi. Mixtures thereof can also be used.

Suitable microorganisms for the inventive method have proven to be in particular bacteria, above all the bacteria of the taxonomic groups:

Alcaligenes, Enterobacteria, Pseudomonas, Bacillus, Lactobacillus, Micrococcus, Staphylococcus, Streptomyces, Cellulomonas, Thiobacillus and Streptococcus.

In particular the following have proved advantageous: *Alcaligenes eutrophus*; Nitrosomonas, Nitrobacter, Nitrococcus, Nitrospira, *Bacillus megaterium, B. mascerans, B. polymyra, B. subtilis, B. stearothermophilus, B. coagulans, B. circulans, B. pasteurii;* Chromatium; *Pseudomonas arvilla, P. putida, P. stutzeri, P. fluorescens, P. denitrificans,* Zoogloea; Zyomonas; Leuconostoc; *Proteus vulgaris; Sporosarcina ureae;* Rhodopseudomonas; Nocardia; Agrobacterium; Cytophaga; Sporocytophaga; Streptomyces; Thiosphaera; Variovorax; Paracoccus; Micromonospora; *Clostridium pectinovorum, C. felsinium;* Azotobacter; Cellulomonas; Azomonas; Rhizobium; Thiobacillus, Thiotrix, Sphaerotilus, Micrococcus; Arthrobacter, Brevibacterium; Photobacterium; Xanthomonas, Acetobacter and Lactobacillus.

*Thiosphaera pantotropha* has proven especially suitable.

Although the abovementioned bacteria show an excellent effect in the inventive method other microorganisms can also be used, namely fungi, from the group of Myxomycetes, Phycomycetes, Ascomycetes, Basidiomycetes and Deuteromycetes, in particular Acrasiales, *Aspergillus niger, A. oryzae, A. wentii; Candida lipoytia,* tropicalis; Saccharomyces; Chaetomium; Cryptococcus.

In a preferred embodiment of the inventive method the bacteria are used in the form of dry bacteria or mixed cultures of dry bacteria.

These mixed cultures of dry bacteria include bacteria such as Aeromonas, Pseudomonas, Bacillus, Lactobacillus, Micrococcus, Streptomyces, Actinomyces, Rhodococcus, Nitrosomonas, Nitrobacter and Thiosphaera.

The microorganisms can generally be added either as dry powder or as liquid slurry. The dry powder can consist only of dried microorganisms, or the latter are mixed with a supporting material or nutrients (Allgemeine Mikrobiologie, Hans G. Schlegel, Seite 174, Thieme Verlag 1985).

The supporting material should be chosen so that it has no negative influence on the properties of the product to be preserved. It can consist of various sugars, water-soluble starch or similar substances. The dry products are optimally first activated by being dispersed in an aqueous medium and then incubated therein for a certain period, e.g. 1 to 10 hours. This suspension with activated microorganisms is then added to the liquid product to be preserved. Alternatively, the dry bacteria can be added directly to the product to be treated.

The microorganisms can also be used in the form of a stabilized liquid product. Such a liquid product is preferably a suspension of spore-forming bacteria like the Bacillus types, or an aqueous suspension of living bacteria at rest that contains substances inhibiting the activation and growth of the bacteria or having a low nutrient offer. Such a liquid product is diluted either in an aqueous medium or in the liquid product to be treated, and thereby activated.

The spores of spore-forming organisms preferably belong to the following aerobic species:

*Bacilli megaterium, B. cercus, B. subtilis, B. lichiniformus, B. anthracis, B. thuringiensis, B. polymyxa, B. mascerans, B. stearothermophilus, B. circulans, B. pasteurii.* They can preferably also belong to the following anaerobic species:

*Saccharolytic clostridia,* including *C. butyricum, C. acetobutyricum, C. Cellulosae dissolvens;* and peptolytic clostridium like *C. Hystolyticum,* and *C. Sporogenes.*

Ureolytic clostridia such as *C. acidiurici* and other spore-forming types such as *Oscillospira guilliermondi.*

The quantity of added bacteria depends on the content of biodegradable substances in the product to be preserved and is advantageously 1 to $10^{10}$ microorganisms per kg of biodegradable substance, but in particular 10 to $10^9$ and very particularly $10^2$ to $10^8$ microorganisms per kg of biodegradable substance. The bacteria preparations in liquid or dry form generally contain $10^6$ to $10^{10}$ bacteria per gram of product.

The invention is based on exploiting the interaction between microorganisms. That is to say, the addition of special bacteria worsens the living conditions for the microorganisms present as contamination. This can be obtained by e.g. direct competition for nutrients, changing the milieu by acidification, production of growth inhibitors, etc. It also follows that for each preservation one must decide which substances are present as contamination and which substances must not be attacked by the microorganisms.

Microorganisms can generally use a number of substances as a substrate, but no microorganism can utilize all organic substrates. This means that e.g. Pseuodomonas can be used where organic substances are employed which cannot be utilized by a certain Pseudomonas species.

Further, certain Pseudomonas species are in a position to produce growth inhibitors for other microorganisms and thereby inhibit them, e.g. *P. acidophila* and *P. mesoacidophila* produce beta-lactam antibiotics, *P. pyrrocinia* yields an antibiotic called pyrrolnitrin, *P. syringae* produces syringotoxin and syringomycin. If all these Pseudomonas species are used this inhibits the microorganisms present as contamination and preserves the organic product.

It is further advantageous in the inventive method to add enzymes additionally to catalyze the degradation of undesirable organic products. Such enzymes can be amylases, proteases, pectinases, cellulases, acylases, aldolases, alkanoxygenases, alcohol dehydrogenases, dehydrogenases, phosphatases, dehydrases, dehydratases, oxygenases, oxidases, lipases, permeases, kinases, carboxylases, phosphorylases, decarboxylases, reductases, oxidoreductases and hemicellulases. Which particular enzyme to use depends on the substances to be eliminated.

The amount of added enzymes is preferably 10 to 10,000 IU per kg total organic carbon (TOC).

Under certain conditions it is further of advantage to add further additives, for example surface-active agents, to the liquid product to be preserved. One can specifically use nonionic surface-active agents and/or lignin sulfonates which are known from European patent 0 185 963. These products can be added to the liquid product to be preserved simultaneously with the added bacteria or singly.

It is further of advantage for suppressing the growth of anaerobic sulfate-reducing bacteria if one additionally adds oxygen to the liquid to be preserved.

The microorganisms and/or other additives and/or oxygen are preferably added in time- or quantity-proportional fashion.

For the treatment of aqueous liquid products one can distinguish two fundamental mechanisms.

1. The principle of treatment is based on the fact that certain selected bacteria have specific nutrient demands. The added microorganisms use the existing nutrients better in competition with the microorganisms present as an impurity, thereby reducing the growth possibilities of the microorganisms already present. Furthermore, undesirable byproducts of the contaminating microorganisms, e.g. hydrogen sulfide, can also be metabolized into harmless final products. A combination of both ways is also possible.

2. The second mechanism of action of the inventive method is the elimination of toxins by the added microorganisms. This prevents the undesirable microorganisms from growing or kills them. The added microorganisms themselves produce no slime or other undesirable byproducts and thus lead to a clear improvement in the stability of the product properties over untreated products.

The added microorganisms are selected according to very specific criteria.

They must have a low tendency to attach to surfaces and form a slime coat, i.e. they must preferably be nonsessile. They should therefore not tend to form colonies or similar aggregates either. To maintain the latter condition it is especially advantageous to add not only the microorganisms to the liquid product to be preserved, but also surface-active agents and/or lignin sulfonates.

The oxygen content in the product to be treated in the initial phase and over a longer period depends on the product and the storage conditions. This and all other information about the susceptibility of the liquid product to be preserved to microbial contamination should be included in the planning of the treatment. Furthermore, one must know of the presence of other compounds which can function as hydrogen acceptors for microbial respiration, such as nitrate.

These substances can be determined analytically and be added if necessary to steer the metabolism of the added or already present bacteria so as to obtain optimal preservation.

It is likewise important how long the corresponding liquid product is to be preserved. Certain bacteria preparations act very efficiently but only for a relatively short period. This is not necessarily a disadvantage, since most biocides are also subject to biodegradation and thus have only a restricted period of action.

In the inventive method the microorganisms are preferably added as a so-called shock dose shortly after production of the product to be preserved. Smaller quantities can subsequently be added just once or at periodical intervals to optimize the treatment.

These time intervals either correspond to pragmatic values or are based on measurements of product properties like hydrogen sulfide content, brightness, pH value and redox potential. For adding the microorganisms it is advisable to use modern metering systems, which detect the actual state in the system with electrodes and use this information to dose the product cost-effectively and efficiently. Enzymes should be added separately from the bacteria in place and time since certain enzymes, such as proteases, damage the added bacteria so that the success of treatment is not guaranteed.

For the same reason hydrogen peroxide, which can be added optionally as an oxygen source, should also be dosed separately or used in a small dose.

The subject of the invention is accordingly also a plant for carrying out the inventive method which is characterized by having a defined metering area in which the microorganisms and any other additives are added to the liquid to be treated either continuously or discontinuously. A metering device is advantageously provided in the metering area for adding the microorganisms as well as additional further metering devices for optionally adding any further additives. The entire metering system preferably works in computer-aided fashion.

The inventive method is advantageously suitable for application in plants in which paper machine broke is taken up, processed, transported or stored. The paper machine broke can exist either as wet broke directly from the wet end of the paper machine or as dry broke, where ready-to-use paper is suspended into a liquid suspension again.

The inventive method is also suitable for application in plants in which pigment fillers in aqueous suspension are produced, processed, taken up, transported or stored. Such suspensions are in particular kaolin slurry, calcium carbonate slurry (ground or precipitated), calcium sulfate slurry (gypsum, ground or deposited or recrystallized) and in particular pigment slurry from paper mills.

A further application of the inventive method is in plants in which starch is produced, processed, taken up, transported, stored or used. Special mention should be made of plants for starch slurries and cooking starch slurries including glue dispersion. The materials can also be organic ones emulsified in water as a colloid, in particular drilling oil, which is used as a coolant or lubricant in metalworking.

The plants can also be ones in which mixtures of mineral and organic substances suspended or emulsified in water are produced, processed, taken up, stored or used, in particular drilling mud, which is used as a lubricant, coolant or production aid in geological wells.

The inventive method is also advantageous in plants in which crude oil emulsions are produced, processed, taken up, stored and used, in particular if saline solutions are used for recovering secondary oils.

It is pointed out explicitly in this connection that the term "plants" is used here to include in particular transport tanks and storage tanks.

The invention will be illustrated in the following with reference to a comparative test.

Two samples of an aqueous solution of paper machine broke were produced. This broke has the following components:

a) Pulp suspension
   Small proportion of groundwood fibers
   Ground calcium carbonate
   Cooked starch
   Production aid
b) Repulped waste paper
   like pulp suspension a) plus
   Pigment (lime, kaolin)
   Latex (styrene-butadiene, acrylic copolymers)
   Optical brightener
   Carboxylmethylcellulose One of the broke samples (sample A) was kept untreated in a sealed canister. The second sample (sample B) was mixed with 50 ppm of a dry product of *Thiosphaera pantotropha* bacteria and likewise kept in a sealed canister.

The storage temperature was an average of 18° C. The pH value of the reference solutions was 7.

After 14 days a partial amount was taken from each of samples A and B and tested for brightness and smell. Brightness was measured on a sheet of paper produced in a sheet forming apparatus.

Result:

| (broke) | Brightness | Smell (paper) | Smell |
|---------|------------|---------------|-------|
| Sample A | gray | musty | rotten eggs |
| Sample B | white | 0 | 0 |

The result shows clearly that the addition of *Thiosphaera pantotropha* produces an excellent preservation effect, in particular on the product-specific properties.

What is claimed is:

1. A method of preserving aqueous solutions or dispersions, said method comprising:
   providing an aqueous solution or dispersion comprising organic substances susceptible to degradation by anaerobically respiring microorganisms;
   adding to said aqueous solution or dispersion living microorganisms that inhibit the growth of said anaerobically respiring microorganisms in said aqueous solution or dispersion;
   whereby said added living microorganisms inhibit growth of said anaerobically respiring microorganisms and prevent degradation of said organic substances in said aqueous solution or dispersion, thereby preserving said aqueous solution or dispersion, said living microorganisms being *Thiospaera pantotropha*.

2. The method of claim 1, wherein the living microorganisms are in a dry form.

3. The method of claim 1 wherein said living microorganisms are suspended in a liquid when added.

4. The method of claim 3, wherein the liquid comprises additives which suppress the metabolism of said living microorganisms.

5. The method of claim 1, wherein a quantity of the living microorganisms based on the quantity of organic substances of the aqueous solution or dispersion to be preserved is 1 to $10^{10}$ microorganisms per kg of total organic carbon (TOC) of the organic substances.

6. The method of claim 1, further comprising adding at least one additive to the solution or dispersion to be preserved, wherein the additive is selected from the group consisting of enzymes, supplines, surface-active agents, lignin sulfonates, and combinations thereof.

7. The method of claim 6, wherein the additive is an enzyme which is added in a concentration of from 10 to 10,000 IU per kg of total organic carbon.

8. The method of claim 1 wherein said anaerobically respiring microorganisms are sulfate-reducing microorganisms.

9. A method of preserving aqueous solutions or dispersions comprising glue or starch, said method comprising:
   providing an aqueous solution or dispersion comprising glue or starch substances that are susceptible to degradation by anaerobic bacteria in said solution or dispersion;
   adding to said aqueous solution or dispersion, living microorganisms that inhibit the growth of said anaerobic bacteria in said aqueous solution or dispersion, wherein said living microorganisms are added to said aqueous solution or dispersion in an amount of from 1 to $10^{10}$ microorganisms per kg of total organic carbon (TOC) of said glue or starch substances in said aqueous solution or dispersion, said living microorganisms being *Thiospaera pantotropha*; and
   adding at least one additive to said aqueous solution or dispersion, where said additive is selected from the group consisting of enzymes, supplines, surfactants, lignin sulfates, and combinations thereof.

10. The method of claim 9 wherein said additive is an enzyme added in a concentration of from 10 to 10,000 IU per kg of total organic carbon (TOC) of said glue or starch substances in said aqueous solution or dispersion.

* * * * *